United States Patent
Doan et al.

(10) Patent No.: US 9,981,134 B2
(45) Date of Patent: *May 29, 2018

(54) MULTI-CHANNEL NEUROMODULATION SYSTEM HAVING FREQUENCY MODULATION STIMULATION

(71) Applicant: Boston Scientific Neuromodulation Corporation, Valencia, CA (US)

(72) Inventors: Que T. Doan, West Hills, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/331,473

(22) Filed: Oct. 21, 2016

(65) Prior Publication Data
US 2017/0036030 A1    Feb. 9, 2017

Related U.S. Application Data

(63) Continuation of application No. 14/859,456, filed on Sep. 21, 2015, now Pat. No. 9,474,905, which is a (Continued)

(51) Int. Cl.
*A61N 1/00* (2006.01)
*A61N 1/36* (2006.01)

(52) U.S. Cl.
CPC ..... *A61N 1/36189* (2013.01); *A61N 1/36071* (2013.01); *A61N 1/36146* (2013.01); (Continued)

(58) Field of Classification Search
CPC ........ A61N 1/36178; A61N 1/32; A61N 1/36; A61N 1/32021; A61N 1/3605; A61N 1/36071
See application file for complete search history.

(56) References Cited

U.S. PATENT DOCUMENTS 6,516,227 B1   2/2003   Meadows et al.
6,895,280 B2   5/2005   Meadows et al.
(Continued)

FOREIGN PATENT DOCUMENTS

| CN | 105163801 A | 12/2015 |
|---|---|---|
| JP | 2016507334 A | 3/2016 |
| WO | WO-2014130858 | 8/2014 |

OTHER PUBLICATIONS

"U.S. Appl. No. 14/186,885, Non Final Office Action dated Feb. 4, 2015", 9 pgs.
(Continued)

*Primary Examiner* — Robert N Wieland
(74) *Attorney, Agent, or Firm* — Schwegman Lundberg & Woessner, P.A.

(57) ABSTRACT

A neuromodulation system comprises a plurality of electrical terminals configured for being respectively coupled to electrodes, modulation output circuitry configured for respectively outputting a plurality of individual electrical pulse trains in a plurality of timing channels to the electrical terminals, wherein each of the timing channels prevents the respective pulse train from having a specific characteristic, and control circuitry configured for controlling the modulation output circuitry in a manner that outputs the pulse trains to a common set of the electrical terminals, thereby creating a combined electrical pulse train at the common set of electrical terminals that has the specific characteristic. A method of providing therapy to a patient comprises delivering a plurality of electrical pulse trains respectively in a plurality of timing channels to a common set of electrodes implanted within the patient, thereby creating a combined electrical pulse train at the common set of electrical terminals.

20 Claims, 8 Drawing Sheets

Related U.S. Application Data continuation of application No. 14/186,885, filed on Feb. 21, 2014, now Pat. No. 9,138,582.

(60) Provisional application No. 61/768,286, filed on Feb. 22, 2013.

(52) U.S. Cl.
CPC ..... *A61N 1/36167* (2013.01); *A61N 1/36171* (2013.01); *A61N 1/36178* (2013.01)

(56) References Cited

U.S. PATENT DOCUMENTS

| | | | |
|---|---|---|---|
| 6,993,384 | B2 | 1/2006 | Bradley et al. |
| 7,539,538 | B2 | 5/2009 | Parramon et al. |
| 9,138,582 | B2 | 9/2015 | Doan |
| 9,474,905 | B2 | 10/2016 | Doan et al. |
| 2003/0139781 | A1 | 7/2003 | Bradley et al. |
| 2005/0267546 | A1 | 12/2005 | Parramon et al. |
| 2006/0259078 | A1 | 11/2006 | Libbus |
| 2010/0274312 | A1 | 10/2010 | Alataris et al. |
| 2011/0040352 | A1 | 2/2011 | Gerber et al. |
| 2011/0160810 | A1* | 6/2011 | Griffith ............... A61N 1/0531 607/72 |
| 2014/0222104 | A1 | 8/2014 | Smith |
| 2014/0243923 | A1 | 8/2014 | Doan et al. |
| 2014/0330345 | A1 | 11/2014 | John |
| 2016/0008604 | A1 | 1/2016 | Doan et al. |

OTHER PUBLICATIONS

"U.S. Appl. No. 14/186,885, Notice of Allowance dated May 22, 2015", 10 pgs.

"U.S. Appl. No. 14/186,885, Response filed May 4, 2015 to Non Final Office Action dated Feb. 4, 2015", 8 pgs.

"U.S. Appl. No. 14/859,456, Non Final Office Action dated Feb. 1, 2016", 9 pgs.

"U.S. Appl. No. 14/859,456, Notice of Allowance dated Jun. 22, 2016", 7 pgs.

"U.S. Appl. No. 14/859,456, Preliminary Amendment filed Oct. 21, 2015", 6 pgs.

"U.S. Appl. No. 14/859,456, Response filed May 2, 2016 to Non Final Office Action dated Feb. 1, 2016", 10 pgs.

"International Application Serial No. PCT/US2014/017777, International Preliminary Report on Patentability dated Sep. 3, 2015", 9 pgs.

"International Application Serial No. PCT/US2014/017777, International Search Report dated May 13, 2014", 6 pgs.

"International Application Serial No. PCT/US2014/017777, Written Opinion dated May 13, 2014", 7 pgs.

\* cited by examiner

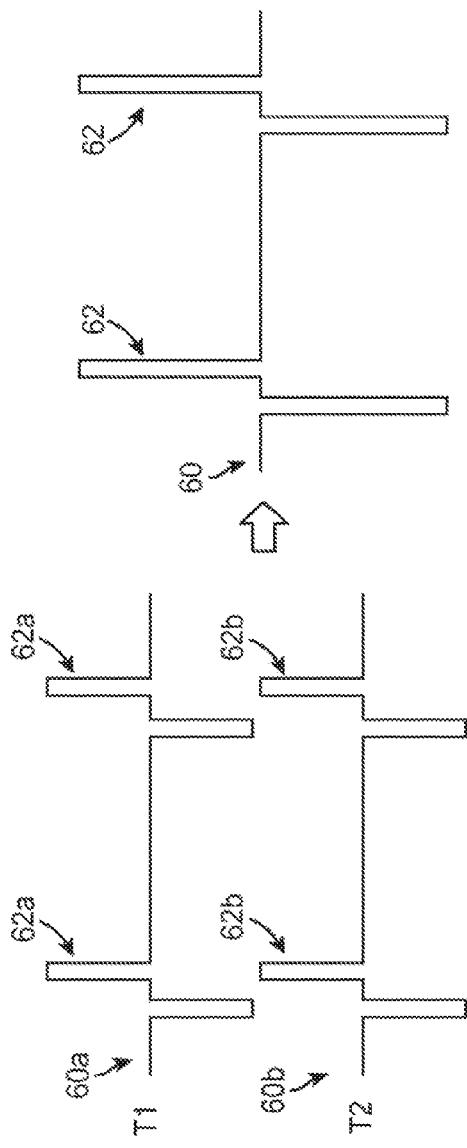
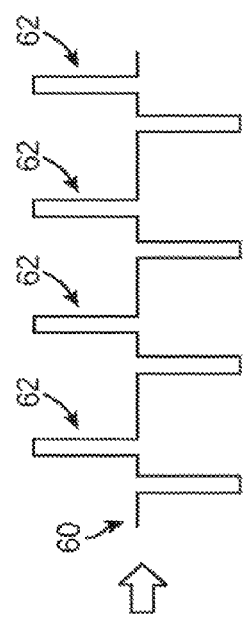
FIG. 6
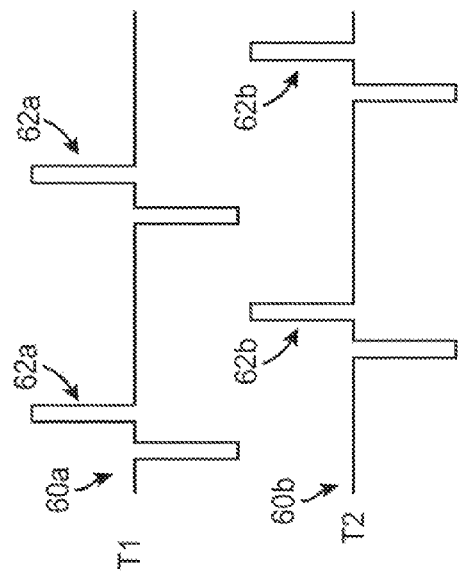
FIG. 7

MULTI-CHANNEL NEUROMODULATION SYSTEM HAVING FREQUENCY MODULATION STIMULATION

RELATED APPLICATION DATA

The present application is a continuation of U.S. application Ser. No. 14/859,456, filed Sep. 21, 2015, now issued as U.S. Pat. No. 9,474,905, which is a continuation of U.S. application Ser. No. 14/186,885, filed Feb. 21, 2014, now issued as U.S. Pat. No. 9,138,582, which claims the benefit under 35 U.S.C. § 119 to U.S. provisional patent application Ser. No. 61/768,286, filed Feb. 22, 2013. The foregoing applications are hereby incorporated by reference into the present application in their entirety.

FIELD OF THE INVENTION

The present invention relates to neuromodulation systems, and more particularly, to multi-channel neuromodulation systems.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neuromodulation systems typically include one or more electrode carrying modulation leads, which are implanted at the desired stimulation site, and a neuromodulator (e.g., an implantable pulse generator (IPG)) implanted remotely from the stimulation site, but coupled either directly to the modulation lead(s) or indirectly to the modulation lead(s) via a lead extension. The neuromodulation system may further comprise an external control device to remotely instruct the neuromodulator to generate electrical modulation pulses in accordance with selected modulation parameters.

Electrical modulation energy may be delivered from the neuromodulator to the electrodes in the form of a pulsed electrical waveform. Thus, modulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, duration, and rate of the electrical pulses provided through the electrode array. Each electrode combination, along with the electrical pulse parameters, can be referred to as a "modulation parameter set."

With some neuromodulation systems, and in particular, those with independently controlled current or voltage sources, the distribution of the current to the electrodes including the case of the neuromodulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neuromodulator to generate electrical modulation pulses in accordance with the selected modulation parameters. Typically, the modulation parameters programmed into the neuromodulator can be adjusted by manipulating controls on the external control device to modify the electrical stimulation provided by the neuromodulator system to the patient. However, the number of electrodes available combined with the ability to generate a variety of complex modulation pulses, presents a vast selection of modulation parameter sets to the clinician or patient.

To facilitate such selection, the clinician generally programs the neuromodulator through a computerized programming system. This programming system can be a self-contained hardware/software system, or can be defined predominantly by software running on a standard personal computer (PC). The PC or custom hardware may actively control the characteristics of the electrical stimulation generated by the neuromodulator to allow the optimum modulation parameters to be determined based on patient feedback or other means and to subsequently program the neuromodulator with the optimum modulation parameter set or sets, which will typically be those that stimulate all of the target tissue in order to provide the therapeutic benefit, yet minimizes the volume of non-target tissue that is stimulated. The computerized programming system may be operated by a clinician attending the patient in several scenarios.

Often, multiple timing channels are used when applying electrical modulation energy to target different tissue regions in a patient. For example, in the context of SCS, the patient may simultaneously experience pain in different regions (such as the lower back, left arm, and right leg) that would require the electrical stimulation of different spinal cord tissue regions. In the context of DBS, a multitude of brain structures may need to be electrically stimulated in order to simultaneously treat ailments associated with these brain structures. Each timing channel identifies the combination of electrodes used to deliver electrical pulses to the targeted tissue, as well as the characteristics of the current (pulse amplitude, pulse duration, pulse rate, etc.) flowing through the electrodes.

As is conventional, the ability of each timing channel to generate modulation energy is typically limited. For example, the maximum pulse amplitude and/or pulse rate that each timing channel can provide may be limited. Furthermore, the nature of the pulse rate for each timing channel may be limited in that it must be uniform. Although these timing channels can be used in combination for providing modulation energy to different tissue regions of a patient, most often, there are restrictions on operating the timing channels together (e.g., the maximum rate of each channel may be limited when multiple timing channels are programmed to operate simultaneously). Furthermore, the timing channels are often operated independent of each other to create separate modulation effects that the different tissue regions. While neuromodulation systems can be designed with hardware capable of addressing these concerns, redesigning the hardware on presently existing neuromodulation designs to accommodate these pulse trains may be a monumental task. Furthermore, neuromodulation systems that are currently used in the field may not be easily updated to eliminate these limitations from the timing channels.

There, thus, remains a need to provide an improved technique for increasing the modulation flexibility of presently existing multi-channel neuromodulation systems.

SUMMARY OF THE INVENTION

In accordance with one aspect of the present inventions, a neuromodulation system comprises a plurality of electrical terminals configured for being respectively coupled to a plurality of electrodes, and modulation output circuitry configured for respectively outputting a plurality of individual electrical pulse trains in a plurality of timing channels to the plurality of electrical terminals. Each of the timing channels prevents the respective pulse train from having a specific characteristic. The neuromodulation system further comprises control circuitry configured for controlling the modulation output circuitry in a manner that outputs the plurality of pulse trains to a common set of the electrical terminals (which may be a single electrical terminal or multiple electrical terminals), thereby creating a combined electrical pulse train at the common set of electrical terminals that has the specific characteristic.

In one embodiment, the specific characteristic is a pulse amplitude that exceeds a maximum value, in which case, the combined electrical pulse train has the pulse amplitude that exceeds the maximum value. In another embodiment, the specific characteristic is a pulse rate that exceeds a maximum value, in which case, the combined electrical pulse train has the pulse rate that exceeds the maximum value. In still another embodiment, the specific characteristic is a varying pulse rate, in which case, the combined electrical pulse train has a varying pulse rate. The pulses of the plurality of pulse trains may be interleaved to create the combined electrical pulse train with the varying pulse rate, or may be sequentially burst to create the combined electrical pulse train with a plurality of burst patterns having different pulse rates.

In an optional embodiment, the neuromodulation system further comprises a user interface configured for receiving an input from a user defining the specific characteristic. In another optional embodiment, the neuromodulation system may further comprise a memory configured for storing a plurality of stimulation programs, in which case, the control circuitry may be configured for programming the plurality of timing channels for each of the stimulation programs. The neurostimulation may further comprise casing containing the plurality of electrical terminals, the modulation output circuitry, and the control circuitry.

In accordance with another aspect of the present inventions, a method of providing therapy to a patient is provided. The method further comprises delivering a plurality of electrical pulse trains respectively in a plurality of timing channels to a common set of electrodes (which may include a single electrode or multiple electrodes) implanted within the patient, thereby creating a combined electrical pulse train at the common set of electrical terminals and providing the therapy to the patient. In one method, the modulation pulses of the plurality pulse trains overlap each other, such that the combined pulse train has a pulse amplitude equal to the sum of the pulse amplitudes of the plurality of pulse trains. In another method, the modulation pulses of the plurality pulse trains are interleaved, such that the combined pulse train has a pulse rate equal to the sum of the pulse rates of the plurality of pulse trains. In still another method, the plurality of pulse trains are sequentially burst to create the combined electrical pulse train with a plurality of burst patterns having different pulse rates. An optional method further comprises receiving input from a user defining a characteristic of the combined pulse train.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 6 is a timing diagram illustrating a first technique for combining pulsed electrical waveforms delivered within multiple timing channels of the IPG of FIG. 3;

FIG. 7 is a timing diagram illustrating a second technique for combining pulsed electrical waveforms delivered within multiple timing channels of the IPG of FIG. 3;

DETAILED DESCRIPTION OF THE EMBODIMENTS

The description that follows relates to a spinal cord modulation (SCM) system. However, it is to be understood that while the invention lends itself well to applications in spinal cord modulation, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neurostimulator configured to treat urinary incontinence, sleep apnea, shoulder sublaxation, headache, etc.

Figure 1:
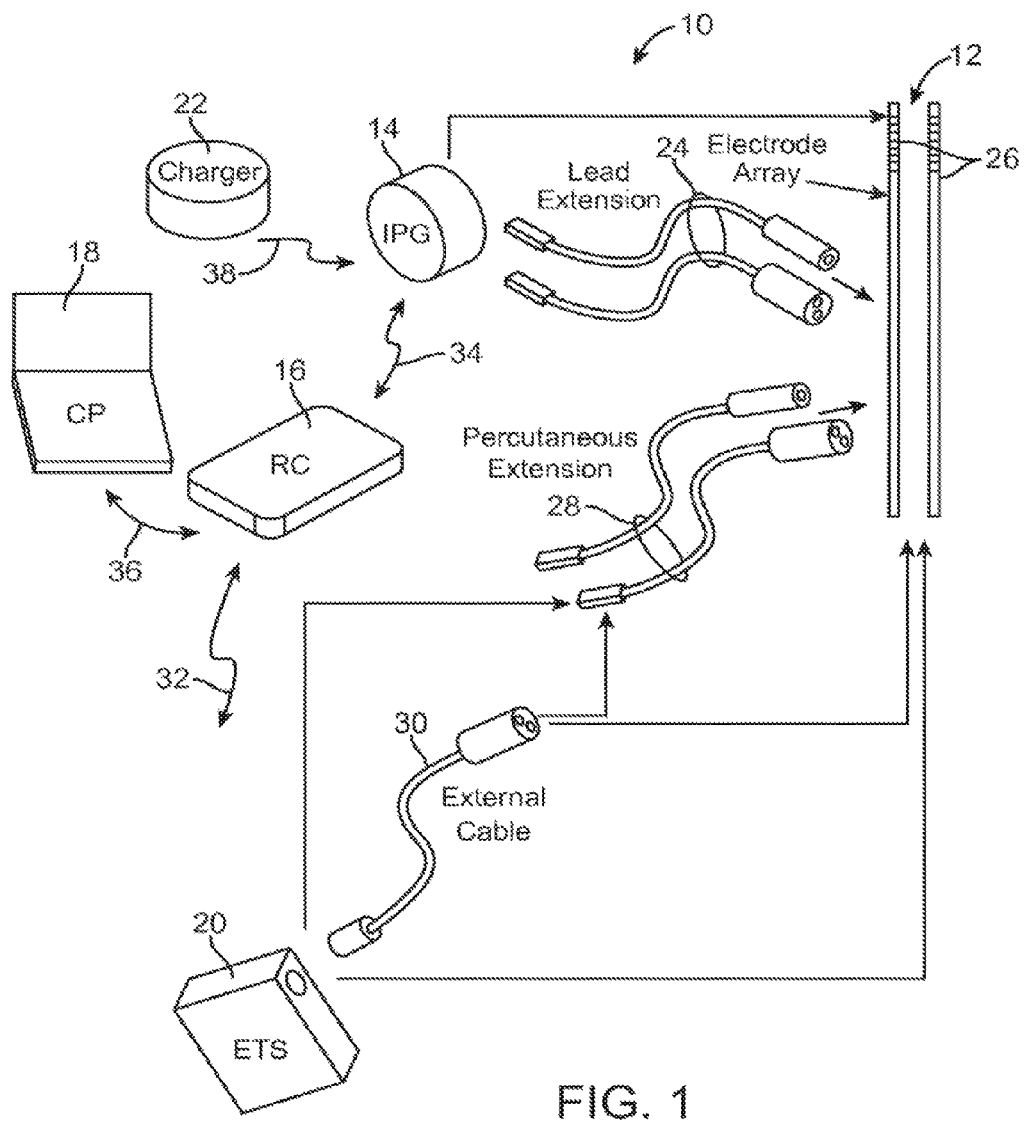
FIG. 1 is a plan view of an embodiment of a spinal cord modulation (SCM) system arranged in accordance with the present inventions.

Turning first to FIG. 1, an exemplary SCM neuromodulation system 10 generally includes one or more (in this case, two) implantable modulation leads 12, an implantable pulse generator (IPG) 14, an external remote controller RC 16, a clinician's programmer (CP) 18, an External Trial Modulator (ETM) 20, and an external charger 22.

The IPG 14 is physically connected via one or more percutaneous lead extensions 24 to the modulation leads 12, which carry a plurality of electrodes 26 arranged in an array. In the illustrated embodiment, the modulation leads 12 are percutaneous leads, and to this end, the electrodes 26 may be arranged in-line along the modulation leads 12. In alternative embodiments, the electrodes 26 may be arranged in a two-dimensional pattern on a single paddle lead. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the modulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the modulation leads 12 have been implanted and prior to implantation of the IPG 14, to test the responsiveness of the stimulation that is to be provided. Thus, any functions described herein with respect to the IPG 14 can likewise be performed with respect to the ETM 20.

The RC 16 may be used to telemetrically control the ETM 20 via a bi-directional RF communications link 32. Once the IPG 14 and modulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. As will be described in further detail below, the CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETM 20, and external charger 22 will not be described herein. Details of exemplary embodiments of these devices are disclosed in U.S. Pat. No. 6,895,280, which is expressly incorporated herein by reference.

Figure 2:
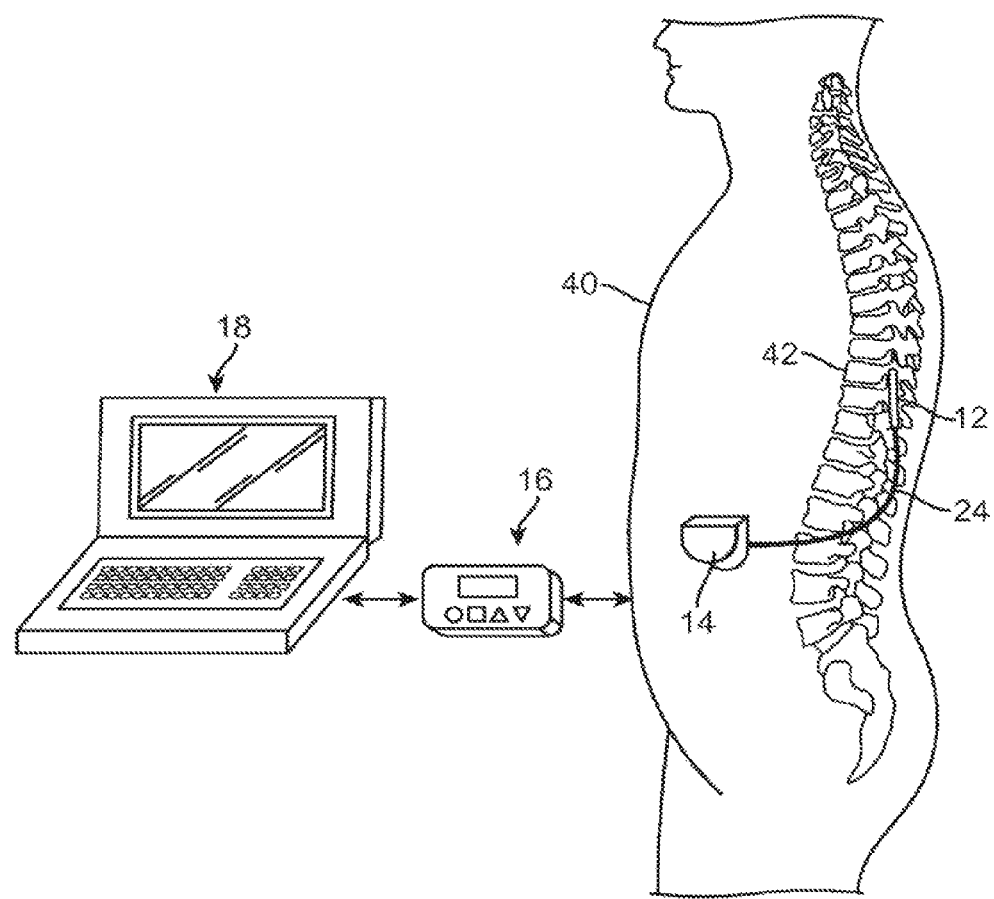
FIG. 2 is a plan view of the SCM system of FIG. 1 in use with a patient.

As shown in FIG. 2, the modulation leads (or lead) 12 are implanted within the spinal column 42 of a patient 40. The preferred placement of the modulation leads 12 is adjacent, i.e., resting near, or upon the dura, adjacent to the spinal cord area to be stimulated. The neuromodulation leads 12 will be located in a vertebral position that depends upon the location and distribution of the chronic pain. For example, if the chronic pain is in the lower back or legs, the modulation leads 12 may be located in the mid- to low-thoracic region (e.g., at the T9-12 vertebral levels). Due to the lack of space near the location where the modulation leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
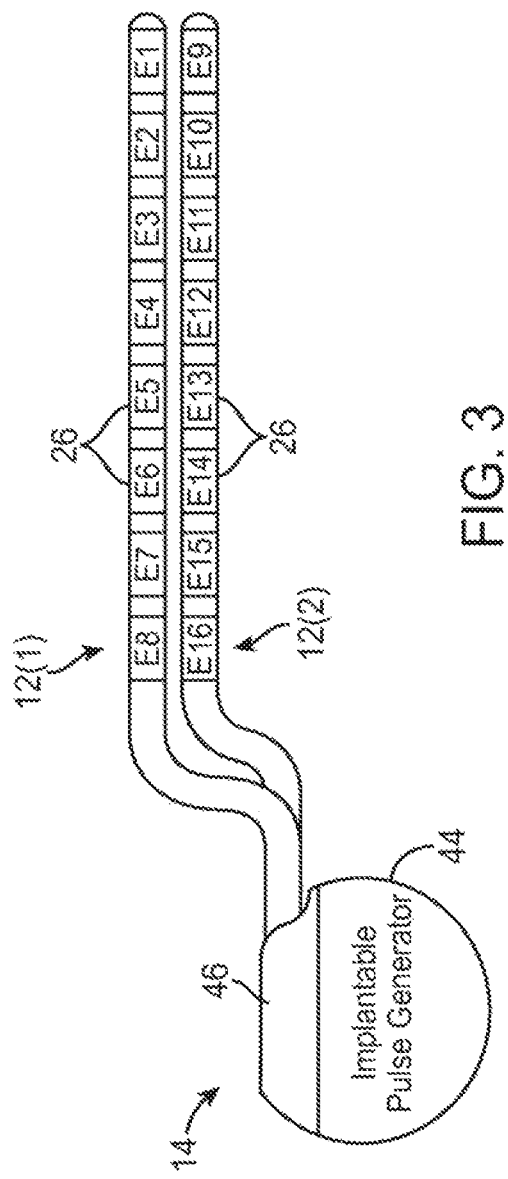
FIG. 3 is a profile view of an implantable pulse generator (IPG) and percutaneous leads used in the SCM system of FIG. 1.

Referring now to FIG. 3, the features of the modulation leads 12 and the IPG 14 will be briefly described. One of the modulation leads 12(1) has eight electrodes 26 (labeled E1-E8), and the other modulation lead 12(2) has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the modulation leads 12 mates in a manner that electrically couples the electrodes 26 to the electronics within the outer case 40. The outer case 44 is composed of an electrically conductive, biocompatible material, such as titanium, and forms a hermetically sealed compartment wherein the internal electronics are protected from the body tissue and fluids. In some cases, the outer case 40 may serve as an electrode.

As will be described in further detail below, the IPG 14 includes a battery and pulse generation circuitry that delivers the electrical modulation energy in the form of one or more electrical pulse trains to the electrode array 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array), pulse duration (measured in microseconds), pulse rate (measured in pulses per second), interphase (measured in microseconds between two phases of a biphasic pulse and burst rate (measured as the modulation on duration X and modulation off duration Y).

Figure 4:
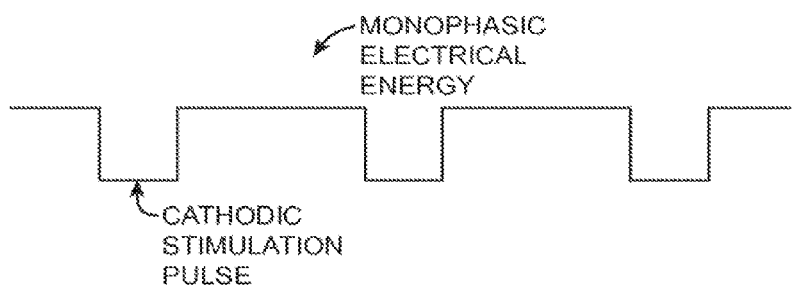
FIG. 4 is a plot of monophasic cathodic electrical modulation energy.

Electrical modulation will occur between two (or more) activated electrodes, one of which may be the IPG case 44. Modulation energy may be transmitted to the tissue in a monopolar or multipolar (e.g., bipolar, tripolar, etc.) fashion. Monopolar modulation occurs when a selected one of the lead electrodes 26 is activated along with the case of the IPG 14, so that modulation energy is transmitted between the selected electrode 26 and case. Bipolar modulation occurs when two of the lead electrodes 26 are activated as anode and cathode, so that modulation energy is transmitted between the selected electrodes 26. For example, electrode E3 on the first lead 12(1) may be activated as an anode at the same time that electrode E11 on the second lead 12(1) is activated as a cathode. Tripolar modulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode The modulation energy may be delivered between a specified group of electrodes as monophasic electrical energy or multiphasic electrical energy. As illustrated in FIG. 4, monophasic electrical energy takes the form of an electrical pulse train that includes either all negative pulses (cathodic), or alternatively all positive pulses (anodic).

Figure 5A:
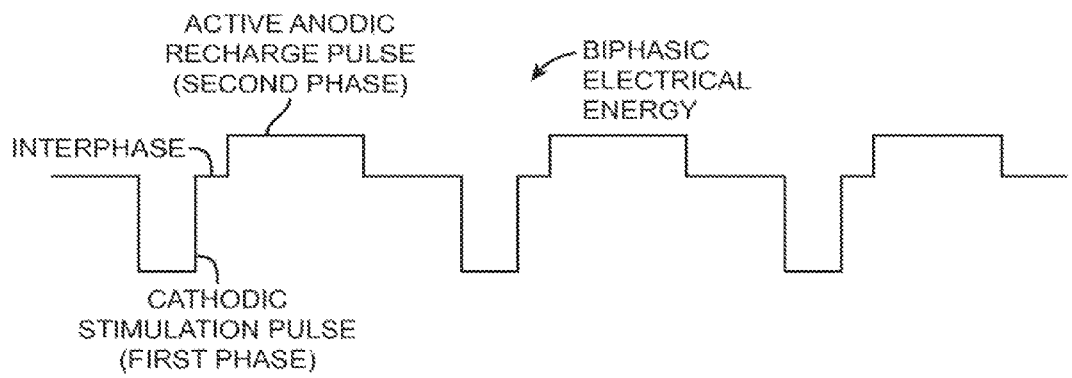
FIG. 5a is a plot of biphasic electrical modulation energy having a cathodic modulation pulse and an active charge recovery pulse.
Figure 5B:
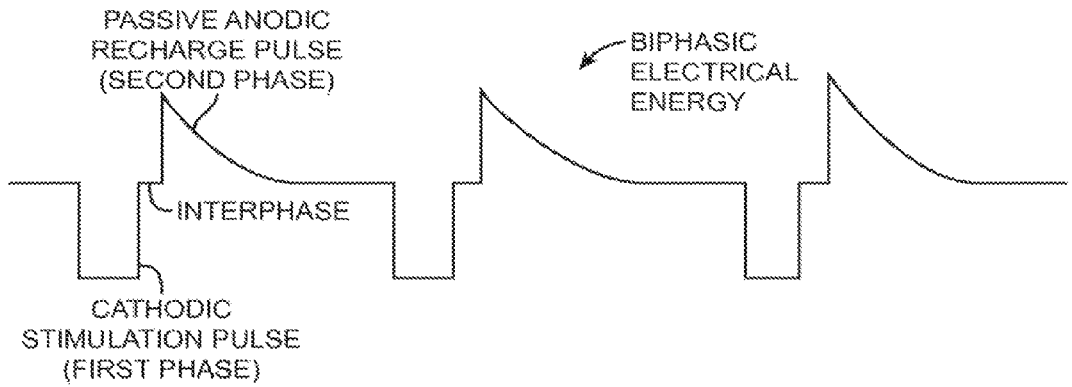
FIG. 5b is a plot of biphasic electrical modulation energy having a cathodic modulation pulse and a passive charge recovery pulse.

Multiphasic electrical energy includes a series of pulses that alternate between positive and negative. For example, as illustrated in FIGS. 5a and 5b, multiphasic electrical energy may include a series of biphasic pulses, with each biphasic pulse including a cathodic (negative) modulation pulse (during a first phase) and an anodic (positive) charge recovery pulse (during a second phase) that is generated after the modulation pulse to prevent direct current charge transfer through the tissue, thereby avoiding electrode degradation and cell trauma. That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the charge recovery pulse).

The second phase may have an active charge recovery pulse (FIG. 5a), wherein electrical current is actively conveyed through the electrode via current or voltage sources, and a passive charge recovery pulse, or the second phase may have a passive charge recovery pulse (FIG. 5b), wherein electrical current is passively conveyed through the electrode via redistribution of the charge flowing from coupling capacitances present in the circuit. Using active recharge, as opposed to passive recharge, allows faster recharge, while avoiding the charge imbalance that could otherwise occur. Another electrical pulse parameter in the form of an interphase can define the time period between the pulses of the biphasic pulse (measured in microseconds).

Significant to the present inventions, the SCM system 10 is capable of concurrently delivering a plurality of individual electrical pulse trains through a respective plurality of timing channels to a common set of electrodes, thereby creating a combined electrical pulse train at the common electrode set. For the purposes of this specification, electrical pulse trains are concurrently conveyed if any of their pulses overlap or are interleaved relative to each other. In a preferred method, the individual pulse trains are respectively conveyed from the plurality of electrodes to the common electrode (or electrodes) via tissue of the patient. Preferably, the tissue adjacent the common electrode (or electrodes) is therapeutically modulated (e.g., stimulated) by the combined electrical pulse train to provide the therapy. Advantageously, using multiple timing channels to combine electrical pulse trains into a single electrical pulse train at a common set of electrodes enables the SCM system 10 to create an electrical pulse train that may not otherwise be able to be created using a single timing channel due to hardware limitations in the SCM system 10.

In particular, the hardware of the SCM system 10 prevents the individual pulse trains conveyed in the respective timing channels from having specific characteristics, which may occur in the combined electrical pulse train. Thus, although the timing channels may prevent the delivery of individual pulse trains having certain characteristics from being delivered to a common set of electrodes, a combined pulse train having such characteristics may be delivered to the common set of electrodes.

For example, the specific characteristic may be a pulse amplitude that exceeds a maximum value (i.e., single channel modulation is limited in that the pulse amplitude of each of the individual pulse trains cannot exceed a maximum value), in which case, the combined electrical pulse train may have the pulse amplitude that exceeds the maximum value. The combined electrical pulse train may be created by overlapping the modulation pulses of the individual pulse trains with each other, such that the combined pulse train has a pulse amplitude equal to the sum of the pulse amplitudes of the individual pulse trains.

As shown in FIG. 6, two individual electrical pulse trains 60a and 60b are respectively delivered in two timing channels T1 and T2 to a common electrode set (e.g., electrode E1) to create a single combined electrical pulse train 60 at the common electrode set. In the illustrated embodiment, the single combined electrical pulse train 60 includes a series of biphasic pulses 62, each of which is created by simultaneously delivering biphasic modulation pulses 62a and 62b of the respective individual electrical pulse trains 60a and 60b to the common electrode set. As shown in FIG. 6, the pulse amplitude of the combined pulse train 60 is greater than the pulse amplitude of either of the individual pulse trains 60a and 60b, and in particular, equal to the sum of the pulse amplitudes of the pulse trains 60a and 60b. In effect, the amplitude of the pulse amplitude of the electrical pulse train delivered to the common set of electrodes is boosted.

As another example, the specific characteristic may be a pulse rate that exceeds a maximum value (i.e., single channel modulation is limited in that the pulse rate of each of the individual pulse trains cannot exceed a maximum value), in which case, the combined electrical pulse train may have the pulse rate that exceeds the maximum value. The combined electrical pulse train may be created by interleaving the modulation pulses of the individual pulse trains with each other, such that the combined pulse train has a pulse rate equal to the sum of the pulse rates of the individual pulse trains.

As shown in FIG. 7, two individual electrical pulse trains 60a and 60b are respectively delivered in two timing channels T1 and T2 to a common electrode set (e.g., electrode E1) to create a single combined electrical pulse train 60 at the common electrode set. In the illustrated embodiment, the single combined electrical pulse train 60 includes a series of biphasic pulses 62, each of which is created by delivering biphasic modulation pulses 62a and 62b of the respective individual electrical pulse trains 60a and 60b to the common electrode set in an interleaving manner. As shown in FIG. 7, the pulse rate of the combined pulse train 60 is greater than the pulse rate of either of the individual pulse trains 60a and 60b, and in particular, equal to the sum of the pulse rates of the pulse trains 60a and 60b. In the illustrated embodiment, the pulse rates of the individual pulse trains 60a and 60b are equal to each other, and thus, the pulse rate of the combined pulse train 60 is uniform and twice the pulse rate of each of the pulse trains 60a and 60b.

As still another example, the specific characteristic may be a varying pulse rate (i.e., single channel modulation is limited in that the pulse rate of each of the individual pulse trains must be uniform), in which case, the combined electrical pulse train may have a varying pulse rate. The combined electrical pulse train may be created by interleaving the modulation pulses of the individual pulse trains with each other, such that the combined pulse train has varying pulse rate.

Figure 8:
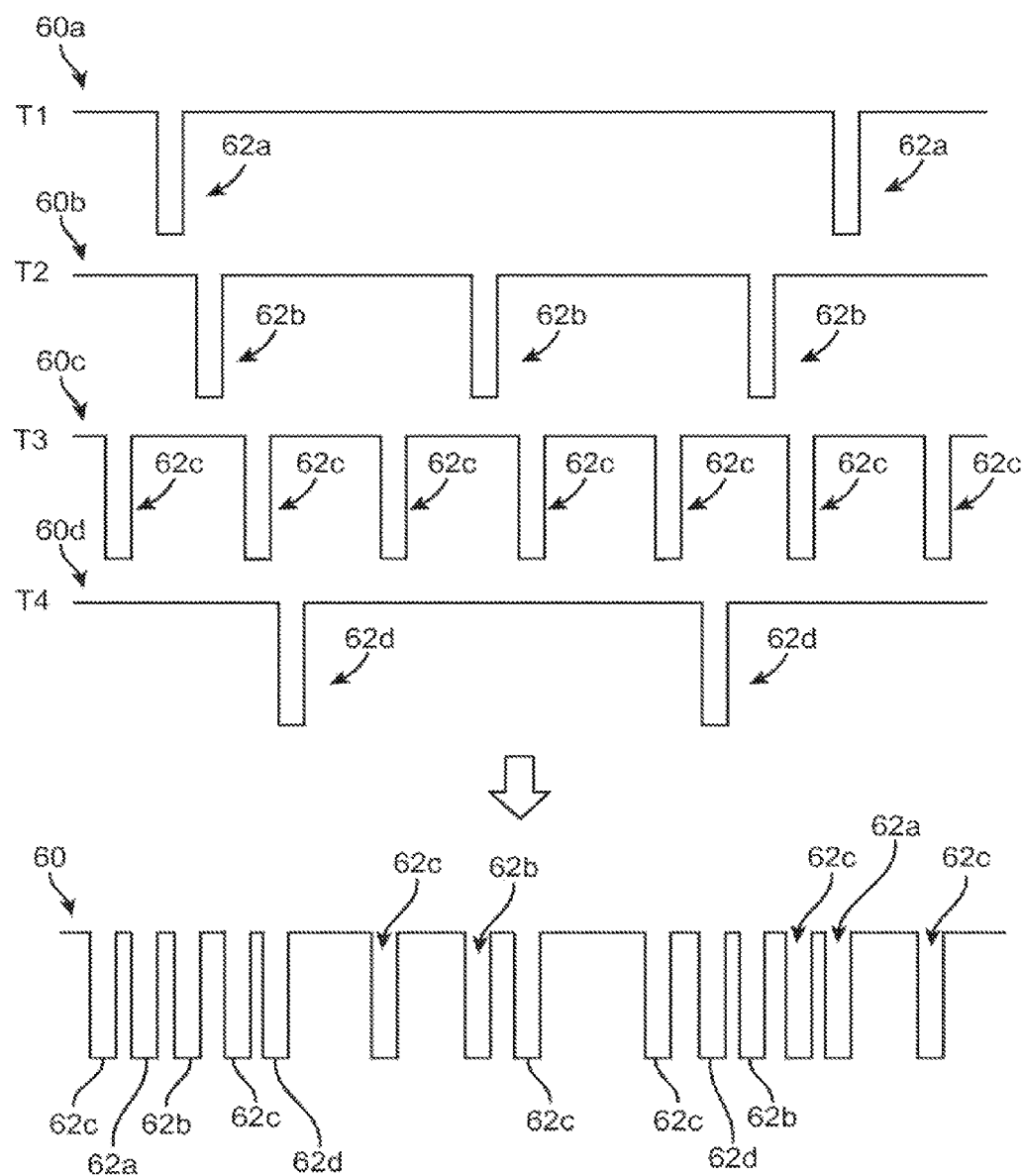
FIG. 8 is a timing diagram illustrating a third technique for combining pulsed electrical waveforms delivered within multiple timing channels of the IPG of FIG. 3.

As shown in FIG. 8, four individual electrical pulse trains 60a-60d are respectively delivered in four timing channels T1-T4 to a common electrode set (e.g., electrode E1) to create a single combined electrical pulse train 60 at the common electrode set. In the illustrated embodiment, the single combined electrical pulse train 60 includes a series of monophasic pulses 62, each of which is created by delivering monophasic modulation pulses 62a-62d of the respective individual electrical pulse trains 60a-60d to the common electrode set in an interleaving manner. As shown in FIG. 8, the pulse rate of the combined pulse train 60 varies between a relatively high level and a relatively low level.

As yet another example, the specific characteristic may be a sequence of bursting patterns having differing pulse rates (i.e., single channel modulation is limited in that each of the individual pulse trains can only be burst on and off with a fixed pulse rate), in which case, the combined electrical pulse train may have a series of bursting patterns with varying pulse rates. In this case, rather than concurrently conveying the electrical pulse trains, as shown in FIGS. 6-8, the electrical pulse trains may be sequentially burst on and off to create a combined electrical pulse train having a plurality of burst patterns with different pulse rates.

Figure 9:
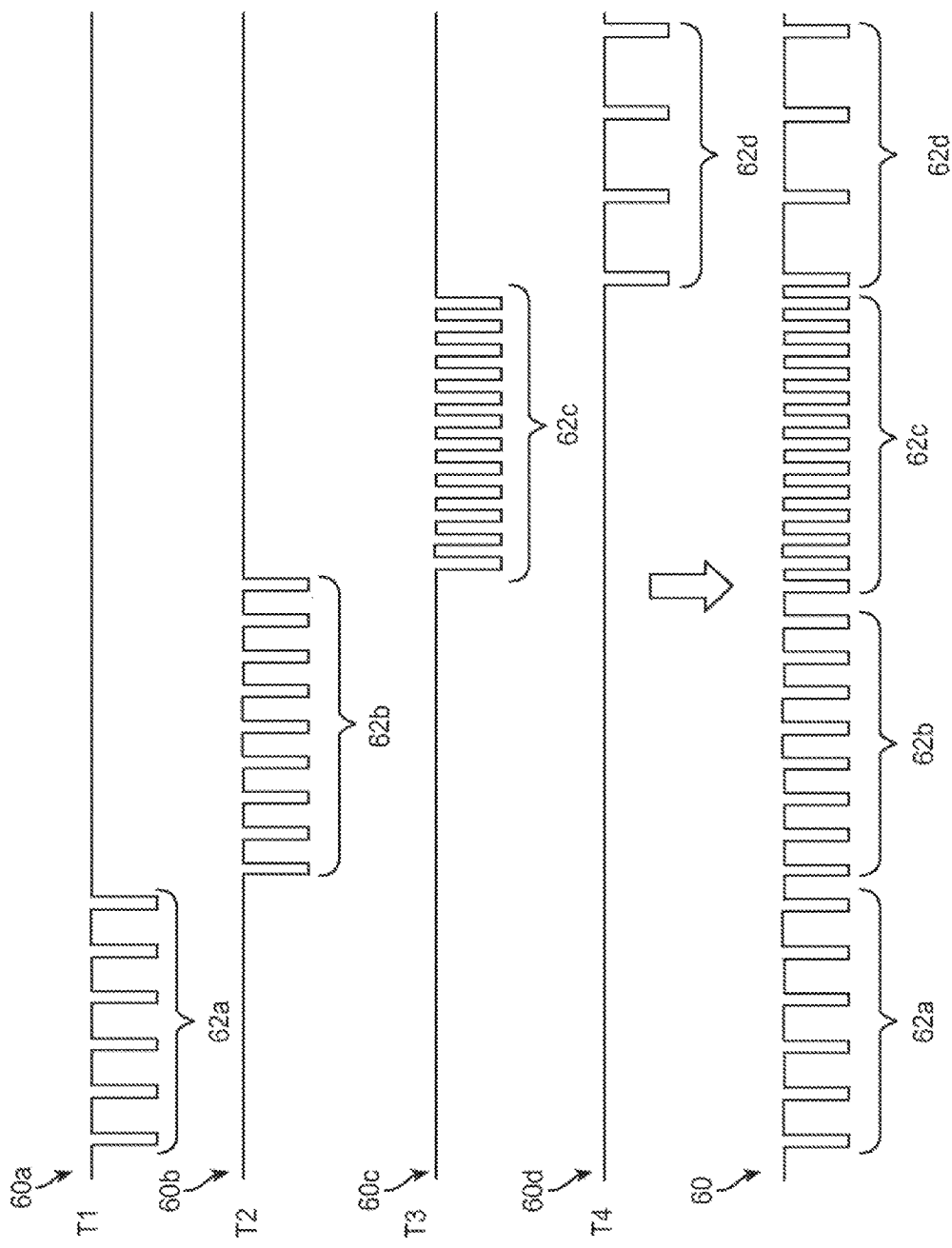
FIG. 9 is a timing diagram illustrating a fourth technique for combining pulsed electrical waveforms delivered within multiple timing channels of the IPG of FIG. 3.

As shown in FIG. 9, four individual electrical pulse trains 60a-60d are respectively delivered in four timing channels T1-T4 to a common electrode set (e.g., electrode E1) to create a single combined electrical pulse train 60 at the common electrode set. In the illustrated embodiment, the single combined electrical pulse train 60 includes a series of pulses 62, each of which is created by sequentially delivering bursts of modulation pulses 62a-62d of the respective individual electrical pulse trains 60a-60d to the common electrode set. As shown in FIG. 9, the combined pulse train 60 includes a first bursting pattern 62a obtained from the first pulse train 60a, then a second bursting pattern 62b obtained from the second pulse train 60b, then a third bursting pattern 62c obtained from the third pulse train 60c, and finally a fourth bursting pattern 62d obtained from the fourth pulse train 60d.

Figure 10:
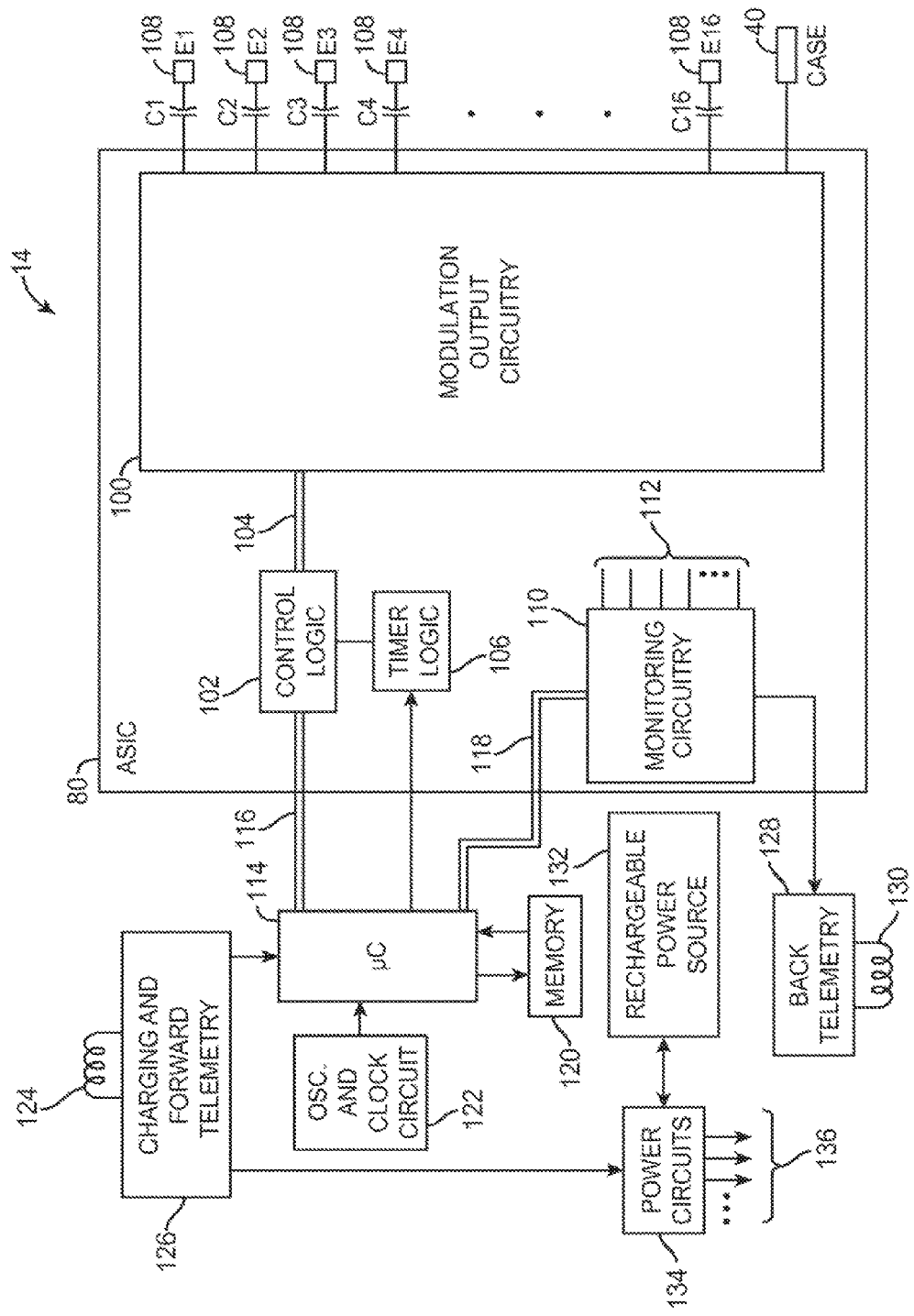
FIG. 10 is a block diagram of the internal components of the IPG of FIG. 3.

Turning next to FIG. 10, the main internal components of the IPG 14 will now be described. The IPG 14 includes modulation output circuitry 100 configured for generating electrical modulation energy in accordance with a defined pulsed waveform having a specified pulse amplitude, pulse rate, pulse width, pulse shape, and burst rate under control of control logic 102 over data bus 104. Control of the pulse rate and pulse width of the electrical waveform is facilitated by timer logic circuitry 106, which may have a suitable resolution, e.g., 10 µs. The modulation energy generated by the modulation output circuitry 100 is output via capacitors C1-C16 to electrical terminals 108 corresponding to the electrodes 26. The analog output circuitry 100 may either comprise independently controlled current sources for providing modulation pulses of a specified and known amperage to or from the electrodes 26, or independently controlled voltage sources for providing modulation pulses of a specified and known voltage at the electrodes 26.

Any of the N electrodes may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary, e.g., as controlled by the RC 16. External programming software in the CP 18 is typically used to set modulation parameters including electrode polarity, amplitude, pulse rate, pulse duration, interphase, bursting rate, and bursting duty cycle for the electrodes of a given channel, among other possible programmable features.

The N programmable electrodes can be programmed to have a positive sourcing current), negative (sinking current), or off (no current) polarity in any of the k channels. Moreover, each of the N electrodes can operate in a multipolar (e.g., bipolar) mode, e.g., where two or more electrode contacts are grouped to source/sink current at the same time. Alternatively, each of the N electrodes can operate in a monopolar mode where, e.g., the electrode contacts associated with a channel are configured as cathodes (negative), and the case electrode (i.e., the IPG case) is configured as an anode (positive).

Further, the amplitude of the current pulse being sourced or sunk to or from a given electrode may be programmed to one of several discrete current levels, e.g., between 0 to 10 mA in steps of 0.1 mA. Also, the pulse duration of the current pulses is preferably adjustable in convenient increments, e.g., from 0 to 1 milliseconds (ms) in increments of 10 microseconds (µs). Similarly, the pulse rate is preferably adjustable within acceptable limits, e.g., from 0 to 1000 pulses per second (pps). Other programmable features can include slow start/end ramping, burst modulation cycling (on for X time, off for Y time), interphase, and open or closed loop sensing modes.

The operation of this analog output circuitry 100, including alternative embodiments of suitable output circuitry for performing the same function of generating modulation pulses of a prescribed amplitude and duration, is described more fully in U.S. Pat. Nos. 6,516,227 and 6,993,384, which are expressly incorporated herein by reference.

The IPG 14 further comprises monitoring circuitry 110 for monitoring the status of various nodes or other points 112 throughout the IPG 14, e.g., power supply voltages, temperature, battery voltage, and the like. The IPG 14 further comprises processing circuitry in the form of a microcontroller (µC) 114 that controls the control logic over data bus 116, and obtains status data from the monitoring circuitry 110 via data bus 118. The IPG 14 additionally controls the timer logic 108. The IPG 14 further comprises memory 120 and oscillator and clock circuitry 122 coupled to the microcontroller 114. The microcontroller 114, in combination with the memory 120 and oscillator and clock circuitry 122, thus comprise a microprocessor system that carries out a program function in accordance with a suitable program stored in the memory 118. Alternatively, for some applications, the function provided by the microprocessor system may be carried out by a suitable state machine.

Thus, the microcontroller 114 generates the necessary control and status signals, which allow the microcontroller 114 to control the operation of the IPG 14 in accordance with a selected operating program and modulation parameters stored in the memory 120. In controlling the operation of the IPG 14, the microcontroller 114 is able to individually generate an electrical pulse train at the electrodes 26 using the modulation output circuitry 100, in combination with the control logic 102 and timer logic 106, thereby allowing each electrode 26 to be paired or grouped with other electrodes 26, including the monopolar case electrode. In accordance with modulation parameters stored within the memory 118, the microcontroller 114 may control the polarity, amplitude, rate, pulse duration and timing channel through which the modulation pulses are provided.

Thus, it can be appreciated that, under control of the microcontroller 114, the modulation output circuitry 100 is configured for outputting a k number of individual electrical pulse trains respectively in a k number of timing channels to the electrical terminals 106, with each electrical pulse train including pulses as shown in FIGS. 4, 5a and 5b. In the IPG 14, up to four stimulation programs may be stored in the memory 120, with each stimulation program having four timing channels. Thus, each modulation program defines four sets of modulation parameters for four respective timing channels. Of course, the IPG 14 may have less or more than four modulation programs, and less or more than four timing channels for each modulation program. Significantly, the microcontroller 114 may control the modulation output circuitry 100 in a manner that delivers multiple electrical pulse trains to a common set of the electrical terminals 108 (and thus, a common set of electrodes 26) to create a single electrical pulse train at the common set of electrical terminals 108; for example, in the manner described in the techniques illustrated in FIGS. 6-9. Because the functions of the microcontroller 114 can be implemented in software, these techniques can be more easily implemented within the IPG 14 without modifying pre-existing hardware designs.

The IPG 14 further comprises an alternating current (AC) receiving coil 124 for receiving programming data (e.g., the operating program and/or modulation parameters) from the RC 16 (shown in FIG. 2) in an appropriate modulated carrier signal, and charging and forward telemetry circuitry 126 for demodulating the carrier signal it receives through the AC receiving coil 124 to recover the programming data, which programming data is then stored within the memory 120, or within other memory elements (not shown) distributed throughout the IPG 14.

The IPG 14 further comprises back telemetry circuitry 128 and an alternating current (AC) transmission coil 130 for sending informational data sensed through the monitoring circuitry 110 to the RC 16. The back telemetry features of the IPG 14 also allow its status to be checked. For example, when the RC 16 initiates a programming session with the IPG 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16, all programmable settings stored within the IPG 14 may be uploaded to the RC 16. Significantly, the back telemetry features allow raw or processed electrical parameter data (or other parameter data) previously stored in the memory 120 to be downloaded from the IPG 14 to the RC 16, which information can be used to track the physical activity of the patient.

The IPG 14 further comprises a rechargeable power source 132 and power circuits 134 for providing the operating power to the IPG 14. The rechargeable power source 132 may, e.g., comprise a lithium-ion or lithium-ion polymer battery. The rechargeable battery 132 provides an unregulated voltage to the power circuits 134. The power circuits 134, in turn, generate the various voltages 136, some of which are regulated and some of which are not, as needed by the various circuits located within the IPG 14. The rechargeable power source 132 is recharged using rectified AC power (or DC power converted from AC power through other means, e.g., efficient AC-to-DC converter circuits, also known as "inverter circuits") received by the AC receiving coil 134. To recharge the power source 132, an external charger (not shown), which generates the AC magnetic field, is placed against, or otherwise adjacent, to the patient's skin over the implanted IPG 14. The AC magnetic field emitted by the external charger induces AC currents in the AC receiving coil 134. The charging and forward telemetry circuitry 136 rectifies the AC current to produce DC current, which is used to charge the power source 132. While the AC receiving coil 134 is described as being used for both wirelessly receiving communications (e.g., programming and control data) and charging energy from the external device, it should be appreciated that the AC receiving coil 134 can be arranged as a dedicated charging coil, while another coil, such as coil 130, can be used for bi-directional telemetry.

It should be noted that the diagram of FIG. 10 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCM system 10 may alternatively utilize an implantable receiver-stimulator (not shown) connected to the modulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the modulation in accordance with the control signals.

As briefly discussed above, the RC 16 and/or CP 18 includes a user interface configured for receiving input from a user to specify the modulation parameters, including the particular electrodes 26 between which the electrical pulse trains are to be delivered. The user may specify a specific characteristic that cannot be achieved using a single timing channel, but can be achieved using multiple timing channels to create a combined electrical pulse train having this specific characteristic, such as those described with respect to FIGS. 6-9.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neuromodulation system to deliver neuromodulation therapy using a patterned electrical waveform output through an electrode, comprising:
   an electrical terminal configured to be electrically coupled to the electrode;
   modulation output circuitry configured to output patterned electrical signals in timing channels to the electrical terminal; and
   control circuitry configured to control the modulation output circuitry to combine the patterned electrical signals at the electrical terminal to provide the patterned electrical waveform, wherein the patterned electrical signals have characteristics that provide the patterned electrical waveform.

2. The neuromodulation system of claim 1, wherein the patterned electrical signals have amplitudes, and the control circuitry is further configured to combine the patterned electrical signals to sum the amplitudes at the electrical terminal to provide the patterned electrical waveform.

3. The neuromodulation system of claim 1, wherein the patterned electrical signals have frequencies that provide a frequency of the patterned electrical waveform.

4. The neuromodulation system of claim 3, wherein the frequency of the patterned electrical waveform is greater than the frequencies of the patterned electrical signals.

5. The neuromodulation system of claim 1, wherein the patterned electrical signals have frequencies selected to provide the patterned electrical waveform with a varying frequency.

6. The neuromodulation system of claim 1, wherein the patterned electrical signals include pulses, and the control circuitry is further configured to control the modulation output circuitry to interleave pulses of the patterned electrical signals.

7. The neuromodulation system of claim 1, wherein the control circuitry is further configured to control the modulation output circuitry to sequentially deliver the patterned electrical signals to create the patterned electrical waveform at the electrical terminal.

8. The neuromodulation system of claim 1, further comprising at least one other electrical terminal configured to be coupled to at least one other electrode, wherein the control circuitry is further configured to control the modulation output circuitry to combine the patterned electrical signals at more than one electrical terminal.

9. The neuromodulation system of claim 1, further comprising a user interface configured to receive an input from a user to define a characteristic of the patterned electrical waveform, and the control circuitry is further configured to control the modulation output circuitry to output patterned electrical signals with characteristics selected to provide the patterned electrical waveform with the characteristic defined by the input from the user.

10. The neuromodulation system of claim 1, wherein the modulation output circuitry is further configured to output multiple patterned electrical signals in multiple timing channels to the electrical terminal.

11. A method of providing neuromodulation therapy using a patterned electrical waveform output through an electrode that is electrically coupled to an electrical terminal, the method comprising:
    outputting the patterned electrical waveform from the electrode, including generating patterned electrical signals in timing channels and combining the patterned electrical signals at the electrical terminal to provide the patterned electrical waveform, wherein the patterned electrical signals have characteristics selected to provide the patterned electrical waveform.

12. The method of claim 11, wherein:
    the patterned electrical signals have amplitudes; and
    the combining the patterned electrical signals includes summing the amplitudes of the patterned electrical signals.

13. The method of claim 11, wherein the patterned electrical signals have frequencies selected to provide a frequency of the patterned electrical waveform.

14. The method of claim 13, wherein the frequency of the patterned electrical waveform is greater than the frequencies of the patterned electrical signals.

15. The method of claim 13, wherein the patterned electrical waveform has a varying frequency.

16. The method of claim 11, wherein:
    the patterned electrical signals include pulses; and
    combining the patterned electrical signals includes interleaving pulses of the patterned electrical signals to provide the patterned electrical waveform at the electrical terminal.

17. The method of claim 11, wherein the combining the patterned electrical signals at the electrical terminal includes sequentially delivering the patterned electrical signals to the electrical terminal.

18. The method of claim 11, further comprising combining the patterned electrical signals at another electrical terminal.

19. The method of claim 11, further comprising receiving an input from a user interface to define a characteristic of the patterned electrical waveform, wherein the patterned electrical signals are generated and combined to provide the patterned electrical waveform with the characteristic defined by the user input.

20. The method of claim 11, wherein the generating the patterned electrical signals in timing channels includes generating patterned electrical signals in multiple timing channels.

* * * * *